United States Patent [19]

Nishiyama et al.

[11] 4,266,064

[45] May 5, 1981

[54] PROCESS FOR PRODUCING CHLORO β-TRIFLUOROMETHYLPYRIDINES

[75] Inventors: Ryuzo Nishiyama, Takatsuki; Kanichi Fujikawa, Moriyama; Isao Yokomichi, Moriyama; Yasuhiro Tsujii, Moriyama; Shigeyuki Nishimura, Shiga, all of Japan

[73] Assignee: Ishihara Sangyo Kaisha Ltd., Osaka, Japan

[21] Appl. No.: 127,468

[22] Filed: Mar. 5, 1980

[51] Int. Cl.$^3$ .............................................. C07D 213/26
[52] U.S. Cl. ...................................................... 546/345
[58] Field of Search .......................................... 546/345

[56] References Cited

U.S. PATENT DOCUMENTS 4,101,554  7/1978  Tobin ..................... 546/345

*Primary Examiner*—Alan L. Rotman
*Attorney, Agent, or Firm*—Oblon, Fisher, Spivak, McClelland & Maier

[57] ABSTRACT

A chloro β-trifluoromethylpyridine is produced by reacting a chloro β-trichloromethylpyridine with hydrogen fluoride in the presence of a specific metal fluoride in a vapor phase at high temperature for a short time. The chloro β-trifluoromethylpyridines which are useful as intermediates for agricultural chemicals and medicines can be obtained at high yield.

5 Claims, No Drawings

PROCESS FOR PRODUCING CHLORO β-TRIFLUOROMETHYLPYRIDINES

BACKGROUND OF THE INVENTION

1. Field of the Invention

The present invention relates to a process for producing mono- and/or di-chloroβ-trifluuoromethylpyridine (hereinafter refered to as the chloroβ-trifluoromethylpyridine) with industrial advantages by fluorinating mono- and/or di-chloroβ-trichloromethylpyridine (hereinafter refered to as the chloroβ-trifluoromethylpyridine) in the presence of a catalyst in a vapor phase.

2. Description of the Prior Arts

Chloroβ-trifluoromethylpyridines have been found to be converted into important compounds having excellent physiological activities and have been considered as important intermediates for agricultural chemicals and medicines. 2-Chloro-5-trifluoromethylpyridine is especially an important intermediate for herbicides, insecticides and fungicides. Therefore, it has been required to find an industrial process for producing such compounds in a mass production and an economical manner.

Thus, not many reports have been found for production of chloroβ-trifluoromethylpyridines, since the utilities of said compounds have not been considered to be important.

A fluorination of the chloroβ-trichloromethylpyridine can be considered for the production of the chloroβ-trifluoromethylpyridine. However, it has been considered that the chloroβ-trichloromethylpyridine as the starting material is not easily produced. For example, it has been described that a chlorination of methyl group of β-picoline is difficult in HELVETICA CHIMICA ACTA, Vol. 59, Fase 1, Nr. 19–20, 1976. Therefore, it has not been known to produce chloroβ-trifluoromethylpyridines in a practical and industrial process.

Recently, it has been proposed to produce said chloroβ-trifluoromethylpyridines in European Pat. No. 0000483 and WO 79/00094 etc. In these prior arts, only experimental small scale processes are disclosed. For example, WO 79/00094 disclosed the following processes for producing 2-chloro-5-trifluoromethylpyridine;

(1) the process of the reaction of 2-chloro-5-trichloromethylpyridine with antimony trifluoride in a liquid phase at 140° to 145° C. for 1 hour;

(2) the process of the reaction of 6-chloronicotinic acid with sulfur tetrafluoride in the presence of hydrogen fluoride in a liquid phase in an autoclave at 120° C. for 8 hours; and (3) the process of the reaction of 2-chloro-5-trichloromethylpyridine with hydrogen fluoride in a liquid phase in an autoclave at 200° C. for 100 hours.

These processes, however, have not been industrially applied for the following reasons: In the process (1) the expensive antimony trifluoride is used and causes trouble in a treatment of a waste solution. In the processes (2), (3), the reactions are respectively carried out under an elevated pressure taking a long reaction time. In the process (2), sulfur tetrafluoride which is toxic to men and beasts is used.

The inventors have studied the fluorination of the chloroβ-trichloromethylpyridine by reacting the chloroβ-trichloromethylpyridine with hydrogen fluoride at elevated temperature in a vapor phase without a catalyst. The desired result has not been accomplished. The inventors have further studies the fluorination by using activated carbon which has been often used in such fluorinations. The desired result has not been also accomplished. The inventors, however, have found the fact that the flouorination is smoothly performed in the presence of a specific catalyst to produce the chloroβ-trifluoromethylpyridine in high yield.

SUMMARY OF THE INVENTION

A first object of the present invention is to provide a process for producing mono- and/or di-chloroβ-trifluoromethylpyridines by using mono- and/or di-chloroβ-trichloromethylpyridines as the starting material with industrial advantages.

A second object of the present invention is to provide a process for producing the chloroβ-trifluoromethylpyridine by reacting the chloroβ-trichloromethylpyridine with hydrogen fluoride in the presence of a specific catalyst in a vapor phase for a short time in high yield.

The other objects of the present invention will be clear by the following description.

The foregoing and other objects of the present invention have been attained by providing a process for producing mono- and/or di-chloroβ-trifluoromethylpyridines selected from the group consisting of 2-chloro-3-trifluoromethylpyridine, 2-chloro-5-trifluoromethylpyridine and 2,6-dichloro-3-trifluoromethylpyridine which comprises reacting mono- and/or di-chloroβ-trichloromethylpyridines selected from the group consisting of 2-chloro-3-trichloromethylpyridine, 2-chloro-5-trichloromethylpyridine and 2,6-dichloro-3-trichloromethylpyridine with hydrogen fluoride in the presence of a catalyst of a fluoride of at least one metal selected from the group consisting of chromium, iron, nickel, manganese, cobalt and aluminum and diluent in a vapor phase at a temperature of 300° to 500° C. for a residence time of 1 to 60 seconds.

DETAILED DESCRIPTION OF THE PREFERRED EMBODIMENTS

The following advantages of the process of the present invention are expected.

(1) The yield of the chloroβ-trifluoromethylpyridine based on the chloroβtrifluoromethylpyridine is as high as 80 to 95%.

(2) The fluorination of the present invention is a simple reaction to perform under the atmospheric pressure for a short time. The reaction can be continuously performed and a reactor can be compact.

(3) The inventors have found an industrial process for producing the chloroβ-trichloromethylpyridine used as the starting material. Hydrogen fluoride and the catalyst are economical and easily available and are not dangerous in the handling thereof.

(4) The chloroβ-trifluoromethylpyridine as the product can be easily separated from the reaction mixture by the conventional purification or separation. The unreacted starting materials and the intermediates can be separated and recovered and reused.

The chloroβtrifluoromethylpyridine includes 2-chloro-3-trichloromethylpyridine, 2-chloro-5-trichloromethylpyridine and/or 2,6-dichloro-3-trichloromethylpyridine.

The catalyst used in the process of the present invention is the specific metal fluoride or a mixture thereof.

The specific metal fluorides include the flourides of chromium, iron, nickel, manganese, cobalt or aluminum such as chromium (II) fluoride ($CrF_2$), chromium (III) fluoride ($CrF_3$), chromium (IV) fluoride ($CrF_4$) as chromium fluorides; iron (II) fluoride ($FeF_2$) and iron (III) fluoride ($FeF_3$) as iron fluorides; nickel (II) fluoride ($NiF_2$); nickel (III) fluoride ($NiF_3$) as nickel fluorides; manganese (II) fluoride ($MnF_2$), manganese (III) fluoride ($MnF_3$), manganese (IV) fluoride ($MnF_4$) as manganese fluorides; cobalt (II) fluoride ($CoF_2$), cobalt (III) fluoride ($CoF_3$), as cobalt fluorides; aluminum (III) fluoride ($AlF_3$) as aluminum fluorides etc.

Among the catalytic components, a fluoride of chromium, iron or aluminum is preferably used for an industrial purpose. It is also preferable to use a composite catalyst obtained by combining an ammonium fluorine compound such as ammonium fluoride, ammonium acidic fluoride as a cocatalyst at a molar ratio of 3 to 20 based on the above-mentioned specific metal fluoride.

As usual, such catalytic component is admixed with a carrier such as activated carbon, activated alumina and aluminum (III) fluoride and the mixture is treated in a form of granules or pellets having a desired size and is fed into the reaction zone. The catalytic component in a form of the specific metal fluoride can be fed into the reactor so as to place it in the reaction zone. It is also possible to feed a precursor of the catalyst in a form of the metal or alloy or the metal oxide, chloride, hydroxide or carbonate or a hydrate thereof, into the reactor and then, to feed hydrogen fluoride gas to react them to form the desired fluoride so as to place it in the reaction zone. For example, a carrier of alumina or aluminum (III) fluoride supporting said precursor such as the specific metal oxide or chloride such as ferric chloride, chromous trioxide and nickel oxide is fed into the reactor and hydrogen fluoride is fed at a reaction temperature of 200° to 500° C. to convert the specific metal compound into the specific metal fluoride before the main reaction.

The process of the present invention can be carried out by any reaction system. The starting materials of the chloro$\beta$-trichloromethylpyridine and hydrogen fluoride can be fed separately or as a mixture into the reaction zone or can be also fed after admixing with diluent. The starting materials can be vaporized, or the chloro$\beta$trifluoromethylpyridine can be dissolved in an inert solvent before vaporizing it.

Suitable diluents include halohydrocarbon type solvents such as carbon tetrachloride, chloroform, methylenechloride, F-112($CFCl_2.CFCl_2$) and F-113 ($CF_2Cl.CFCl_2$); and inert gases such as nitrogen, argon and helium.

The amount of the diluent is not critical. The diluent is usually used at a molar ratio of 1 to 20, preferably 3 to 10, based on the chloro$\beta$trifluoromethylpyridine. The amount of hydrogen fluoride is not critical, hydrogen fluoride is usually used at a molar ratio of 3 to 10, preferably 4 to 9, based on the chloro$\beta$trifluoromethylpyridine.

The process of the present invention can be carried out by any reaction system, however, it is practically preferable to perform the reaction in the presence of a fixed bed or a fluidized bed of the solid catalyst in the reaction zone. It is optimum to perform the reaction by fluidizing a suspension of the solid catalyst in a mixed gas containing the starting materials of the chloro$\beta$-trichloromethylpyridine and hydrogen fluoride, the diluent, the reaction product, and hydrogen chloride.

The reaction of the chloro$\beta$-trichloromethylpyridine with hydrogen fluoride is usually carried out at a temperature of 300° to 500° C., preferably 350° to 450° C., for a residence time of 1 to 60 seconds preferably 1 to 20 seconds.

The gaseous reaction mixture obtained by the fluorination is discharged from the reactor. The gaseous reaction mixture contains fluorinated products including the chloro$\beta$-trifluoromethylpyridine as the main product and the unreacted hydrogen fluoride, hydrogen chloride as by-product and the diluent. The reaction mixture is treated by suitable cooling and condensing apparatus to liquefy the fluorinated products to obtain a liquid mixture containing the chloro$\beta$-trifluoromethylpyridine as the main component. The liquid mixture is purified by the conventional processes such as an extraction, a distillation and a crystallization to separate the chloro$\beta$trifluoromethylpyridine at high yield, such as more than 80% based on the chloro$\beta$-trichloromethylpyridine.

The resulting chloro$\beta$-trifluoromethylpyridines obtained by the process of the present invention include 2-chloro-3-trifluoromethylpyridine, 2-chloro-5-trifluoromethylpyridine or 2,6-dichloro-3-trifluoromethylpyridine or a mixture thereof.

When intermediates substituting one or two chlorine atoms of the trichloromethyl group of the chloro$\beta$-trichloromethylpyridine to fluorine atoms are included together with the chloro$\beta$-trifluoromethylpyridine in the fluorinated product, such intermediates can be separated with the unreacted starting materials and the diluent, and are recovered and recycled into the reaction zone.

The present invention will be further illustrated by certain examples and references which are provided for purposes of illustration only and are not intended to be limiting the present invention.

EXAMPLE 1

A stainless steel reaction tube having an inner diameter of 42 mm and a length of 1250 mm as a reaction zone was used. The part from the inlet to 250 mm of the reaction tube was used as a catalyst packed part. A stainless steel preheating tube having an inner diameter of 20 mm and a length of 500 mm was used for a preheating of hydrogen fluoride. A heat resisting glass (Pyrex) preheating tube having an inner diameter of 30 mm and a length of 500 mm was used for a preheating of the chloro$\beta$-trichloromethylpyridine.

The reaction tube and the preheating tubes were each covered by an electric heater and an insulator so as to control the temperature outwardly and they were respectively placed in slant positions.

A homogeneous mixture of a catalyst powder of 0.02 mole of chromium (III) fluoride hydrate ($CrF_3.3H_2O$), 0.1 mole of ammonium acid fluoride ($NH_4F.HF$) and 0.1 mole of ammonium fluoride ($NH_4F$) and 40 g. of granular activated carbon was packed into the catalyst packing part. The reaction tube was heated at 350° C. and hydrogen fluoride was passed at a rate of 1 g/min. for 2 hours. Then, 277 g. (1.2 mole) of 2-chloro-5-trichloromethylpyridine, 554 g. (3.6 mole) of carbon tetrachloride and 192 g. (9.6 mole) of hydrogen fluoride which were preheated at 300° C., were fed at constant flow rates for 65 minutes to react them in a vapor phase at 350° C. The residence time of the reaction mixture in the reaction zone was about 9 seconds.

The gas discharged from the reaction tube was condensed by passing it through a water scrubbing column and a caustic alkali scrubbing column. The condensed solution was separated and washed with water and dehydrated over sodium sulfate and then, carbon tetrachloride was distilled off under a reduced pressure to obtain 242 g. of an oily product. The oily product was analyzed by gas chromatography with a temperature reprogrammer. The ratio of the object compound of 2-chloro-5-trifluoromethylpyridine to the recovered organic materials was 94% and the yield of the object product after the distillation and the purification was 89.5%.

The recovered organic materials include the object products as well as 20% of 2-chloro-5-fluorodichloromethylpyridine and 6.7% of 2-chloro-5-chlorodifluoromethylpyridine as intermediates and 3.8% of the unreacted 2-chloro-5-trichloromethylpyridine.

EXAMPLE 2

In accordance with the process of Example 1 except using 0.02 mole of iron (II) fluoride hydrate ($FeF_2.8H_2O$) instead of 0.02 mole of chromium (III) fluoride hydrate, a reaction and a purification were carried out to obtain the object product of 2-chloro-5-trifluoromethylpyridine at a conversion of 93% in a yield of 86.5%. As an intermediate 4% of 2-chloro-5-chlorodifluoromethylpyridine was recovered.

EXAMPLE 3

In accordance with the process of Example 1 except using 0.02 mole of nickel (II) fluoride hydrate ($NiF_2.3H_2O$) instead of 0.02 mole of chromium (III) fluoride hydrate, a reaction and a purification were carried out to obtain the object product of 2-chloro-5-trifluoromethylpyridine at a conversion of 85% in a yield of 80.1%.

As an intermediate, 10% of 2-chloro-5-chlorodifluoromethylpyridine was recovered.

EXAMPLE 4

A vertical reaction tube made of Inconel having a reaction zone of a catalyst fluidized bed (an inner diameter of 151 mm and a height of 1440 mm) was used as a reactor. Two preheating tubes made of Inconel having an inner diameter of 40 mm and a length of 1500 mm for the starting materials and the diluent were connected to the reaction tube. The reaction tube and the preheating tubes were each covered by an electric heater and an insulator so as to control the temperature outwardly. A composition obtained by thoroughly mixing 970 g. of chromium (III) fluoride hydrate and 12 kg. of activated alumina having a particle diameter of 0.18 to 0.4 mm was packed into the catalyst packing part. The reaction tube was heated at 430° C. and hydrogen fluoride was fed at a rate of 20 liter/min. for 3 hours to activate the catalyst.

The reactor was heated at 430° C. and 2-chloro-5-trichloromethylpyridine was fed at a rate of 101.6 g/min. and nitrogen gas was fed at a rate of 64 liter/min. through one preheating tube and hydrogen fluoride was fed at a rate of 39 liter/min. through the other preheating tube. They were respectively fed into the reaction tube as the mixed gases at about 200° C. to react them for about 70 hours. The activated catalyst was continuously fed and discharged at a rate of 3 kg./hour. The residence time of the reaction mixture in the reaction zone was about 5.4 seconds.

The gas discharged from the reactor was condensed by passing it through a water scrubbing column and a caustic alkali scrubbing column. The resulting oily product was separated and washed with water to obtain 360 kg. of the oily product containing chloro$\beta$-trifluoromethylpyridines. The oily product was distilled to obtain 287 kg. of the object product of 2-chloro-5-trifluoromethylpyridine (yield of 86%).

The residue obtained by separating the object product was 36 kg. of a mixture containing 10.2% of 2-chloro-5-trifluoromethylpyridine, 38.2% of chloro-5-chrorodifluoromethylpyridine, 43.2% of 2-chloro-5-fluorodichloromethylpyridine and the unreacted 2-chloro-5-trichloromethylpyridine.

EXAMPLE 5

In accordance with the process of Example 4 except using 1840 g. of anhydrous ferric fluoride instead of 970 g. of chromium (III) fluoride hydrate, a reaction and a purification were carried out. The results were substantially the same.

In accordance with the process of Example 4 except using manganese (II) fluoride as a manganese fluoride or cobalt (III) fluoride as a cobalt fluoride instead of the chromium (III) fluoride hydrate, each reaction was carried out. The results were substantially the same.

EXAMPLE 6

In accordance with the process of Example 4 except feeding 2, 6-dichloro-3-trichloromethylpyridine at a rate of 117 g/min. instead of the feed of 2-chloro-5-trichloromethylpyridine at a rate of 101.6 g/min. and varying the residence time of the reaction mixture from 5.4 seconds to 5.2 seconds, a reaction and a purification were carried out to obtain 417 kg. of the object product of 2, 6-dichloro-3-trifluoromethylpyridine (yield of 85%).

We claim:

1. A process for producing a chloro$\beta$-trifluoromethylpyridine selected from the group consisting of 2-chloro-3-trifluoromethylpyridine, 2-chloro-5-trifluoromethylpyridine and 2, 6-dichloro-3-trifluoromethylpyridine which comprises reacting a chloro$\beta$-trichloromethylpyridine selected from the group consisting of 2-chloro-3-trichloromethylpyridine, 2-chloro-5-trichloromethylpyridine and 2, 6-dichloro-3-trichloromethylpyridine with hydrogen fluoride in the presence of a catalyst of a fluoride of at least one metal selected from the group consisting of chromium, iron, nickel, manganese, cobalt and aluminum and diluent in a vapor phase at a temperature of 300° to 500° C. for a residence time of 1 to 60 seconds.

2. A process according to claim 1 wherein said catalyst is a fluoride of chromium, iron or aluminum.

3. A process according to claim 1 wherein said reaction temperature is in a range of 350° to 450° C.

4. A process according to claim 1 wherein said residence time of the reaction mixture is in a range of 1 to 20 seconds.

5. A process according to claim 1 wherein a solid catalyst is suspended in a gas flow containing said diluent, said starting material, said reaction product and hydrogen chloride to react said chloro$\beta$-trichloromethylpyridine with hydrogen fluoride in a fluidized condition.

* * * * *

UNITED STATES PATENT AND TRADEMARK OFFICE
CERTIFICATE OF CORRECTION

PATENT NO. : 4,266,064
DATED : May 5, 1981
INVENTOR(S) : RYUZO NISHIYAMA ET AL

It is certified that error appears in the above—identified patent and that said Letters Patent is hereby corrected as shown below:

Please correct the Priority Data to read as follows:

[30]--Foreign Application Priority Data

Mar. 19,1979 [JP] Japan ...... 54-32067

Jan. 14,1980 [JP] Japan ...... 55-2974

Signed and Sealed this

Twenty-first Day of July 1981

[SEAL]

Attest:

GERALD J. MOSSINGHOFF

Attesting Officer     Commissioner of Patents and Trademarks